(12) United States Patent
    Lin

(10) Patent No.: US 10,633,747 B2
(45) Date of Patent: Apr. 28, 2020

(54) GAS GENERATOR

(71) Applicant: Hsin-Yung Lin, Shanghai (CN)

(72) Inventor: Hsin-Yung Lin, Shanghai (CN)

(*) Notice: Subject to any disclaimer, the term of this patent is extended or adjusted under 35 U.S.C. 154(b) by 0 days.

(21) Appl. No.: 16/219,132

(22) Filed: Dec. 13, 2018

(65) Prior Publication Data

US 2019/0112718 A1    Apr. 18, 2019

Related U.S. Application Data

(63) Continuation of application No. 15/639,142, filed on Jun. 30, 2017, now Pat. No. 10,190,223.

(30) Foreign Application Priority Data

Jun. 30, 2016    (TW) .................................. 105120684
Jun. 27, 2017    (CN) ............................ 201710498662

(51) Int. Cl.
    *C25B 1/02*    (2006.01)
    *C25B 13/02*   (2006.01)
    *C25B 13/04*   (2006.01)
    *C25B 7/00*    (2006.01)
    *A61M 16/16*   (2006.01)
    *A61M 16/10*   (2006.01)
    *A61M 16/20*   (2006.01)

(52) U.S. Cl.
    CPC ............... *C25B 1/02* (2013.01); *A61M 16/10* (2013.01); *A61M 16/165* (2014.02); *C25B 7/00* (2013.01); *C25B 13/02* (2013.01); *C25B 13/04* (2013.01); *A61M 16/106* (2014.02); *A61M 16/201* (2014.02); *A61M 2205/21* (2013.01)

(58) Field of Classification Search
    CPC ........... C25B 1/02; C25B 13/02; C25B 13/04; A61M 16/10; A61M 16/106
    See application file for complete search history.

(56) References Cited

U.S. PATENT DOCUMENTS 10,190,223  B2 *  1/2019  Lin ..................... A61M 16/10

FOREIGN PATENT DOCUMENTS

| CN | 102068743 | 5/2011 |
|----|-----------|--------|
| CN | 203613264 | 5/2014 |
| TW | M483791   | 8/2014 |
| TW | M485391   | 9/2014 |
| TW | 201615895 | 5/2016 |

* cited by examiner

*Primary Examiner* — Arun S Phasge

(57) ABSTRACT

The present invention provides a gas generator and comprises an electrolytic cell and a water-blocking device. The electrolytic cell is used for electrolyzing electrolyzed water to generate a gas with hydrogen. The electrolytic cell has an outlet for outputting the gas with hydrogen. The water-blocking device is set on the outlet for preventing the electrolyzed water from flowing out when the electrolytic cell is tilted by a tilt angle. The gas pathway of the invention will be closed by the water-blocking device when the gas generator is toppled, thereby preventing the electrolyte-rich electrolyzed water from flowing out.

7 Claims, 8 Drawing Sheets

GAS GENERATOR

CROSS-REFERENCE TO RELATED APPLICATIONS

This application is a continuation of U.S. application Ser. No. 15/639,142, filed Jun. 30, 2017 which claims the priority benefit of Taiwan Application No. 105120684 filed Jun. 30, 2016 and Chinese Application No. 201710498662.X, filed Jun. 27, 2017 the disclosure of which are incorporated herein by reference.

BACKGROUND OF THE INVENTION

1. Field of the Invention

The present invention relates to a gas generator, and more particularly, the present invention relates to a gas generator with a water-blocking device for closing a gas pathway when the gas generator is toppled.

2. Description of the Prior Art

People are always paying a great deal of attention on health developments. Many developments in medical technology are often targeted on treating diseases and prolonging human life. However, most of the treatments in the past are passive, which means the diseases are only treated as they occur. These methods include operation, medication, radiation therapy, chronic diseases care, rehabilitation, corrective therapy, or even medical treatments for cancers. In recent years, the research from medical experts has been gradually moving towards preventive medical methods, such as research on healthy food, screening and preventing inherited diseases, which actively prevents diseases from occurring in the future. Because of the focus on prolonging human life, many anti-aging and anti-oxidation technologies including skin care products and anti-oxidation food/medicine are gradually being developed and are becoming increasingly popular to the general public.

Studies have found that there are instable oxygen species (O+), also known as free radicals, in the human body. The free radicals are usually generated due to diseases, diet, environment and one's lifestyle, but they can be excreted in the form of water by reacting with the inhaled hydrogen. With this method, the amount of free radicals in the human body can be reduced, thereby restoring the body condition from an acidic state to an alkaline state, achieving an anti-oxidation, anti-aging and beauty health effect, and even eliminating chronic diseases. Furthermore, there are many clinical experiments showing that patients who need to inhale a high concentration of oxygen for an extended period of time would experience lung damage, and they could be ameliorated by inhaling hydrogen.

Hydrogen gas is generally generated through electrolyzing liquid water by an electrolytic apparatus for humans to breathe. However, it is dangerous for humans to breathe the electrolyte-rich electrolyzed water if the electrolytic apparatus does not make the gas pathway closed when the electrolytic apparatus is toppled.

SUMMARY OF THE INVENTION

Therefore, the present invention is to provide a gas generator for electrolyzing liquid water and generating a gas with hydrogen. Meanwhile, the gate of the electrolytic cell will be closed to prevent the electrolyzed water from flowing out of the electrolytic cell when the gas generator is toppled.

The present invention provides a gas generator comprising an electrolytic cell and a water-blocking device. The electrolytic cell contains electrolyzed water, wherein the electrolyzed water includes an electrolyte. The electrolytic cell is used for electrolyzing the electrolyzed water to generate a gas with hydrogen, and the electrolytic cell has an outlet for outputting the gas with hydrogen. The water-blocking device is configured on the outlet, wherein the water-blocking device is used for preventing the electrolyzed water from flowing out of the electrolytic cell when the electrolytic cell is tilted by a tilt angle, wherein the tilt angle is over than 90 degrees.

The water-blocking device comprises a bottom and a leakproof part, the bottom has an inlet for receiving the gas with hydrogen, and the inlet is closed selectively by the leakproof part for preventing the electrolyzed water from flowing out of the electrolytic cell. The bottom further has an elastic plug, and the leakproof part has a plug hole, and the elastic plug is coupled with the plug hole to make the inlet to be closed selectively by the leakproof part for preventing the electrolyzed water from flowing out of the electrolytic cell.

The gas generator further comprises a humidification device connected to the water-blocking device for receiving the gas with hydrogen, wherein the humidification device comprises a cooling filter element for cooling the gas with hydrogen and generating a filtered gas with hydrogen by filtering out an impurity from the gas with hydrogen. The humidification device has a shell contains a humidification liquid, and the humidification device further comprises an intake element coupled with the cooling filter element for passing the filtered gas with hydrogen into the humidification liquid. Furthermore, the intake element comprises an inlet screen for further filtering the filtered gas with hydrogen before the filtered gas with hydrogen being passed into the humidification liquid, wherein the inlet screen can be a unidirectional screen to prevent the humidification liquid from flowing into the intake element.

The gas generator further comprises a float contained in the shell, wherein the shell has a water charging channel for charging the humidification liquid; the water charging channel will be blocked by the float when a level of the humidification liquid in the shell is higher than a predetermined height. Furthermore, the water charging channel has an outward tapering portion, a minimum inner diameter of the portion is smaller than a maximum outer diameter of the float. In addition, the shell has a space for limiting a movement of the float, then the float is restricted to move longitudinally in the space according to the level of the humidification liquid to block the water charging channel.

The gas generator further comprises an atomizing device connected to the humidification device for receiving the filtered gas with hydrogen. The atomizing device further generates an atomized gas to be mixed with the filtered gas with hydrogen to generate a healthy gas, wherein the atomized gas is selected from a group comprising water vapor, an atomizing solution, a volatile essential oil, and any combination thereof.

The gas generator further comprises a float contained in the electrolytic cell, and the electrolytic cell has a water charging channel for charging the electrolyzed water; wherein the water charging channel will be blocked by the float when a level of the electrolyzed water in the electrolytic cell is higher than a predetermined height. Furthermore, the water charging channel is connected to the outlet. In conclusion, the priority of the present invention is to provide a gas generator, comprising an electrolytic cell and a humidification device. In the gas generator of the present invention, the electrolytic cell is used for electrolyzing electrolyzed water to generate a gas with hydrogen, and the humidification device is used for filtering and humidifying the gas with hydrogen to provide humans to breathe, wherein the gate of the electrolytic cell will be closed to prevent the electrolyzed water from flowing out of the electrolytic cell when the gas generator is toppled.

The advantages and spirits of the invention may be understood by the following recitations together with the appended drawings.

BRIEF DESCRIPTION OF THE APPENDED DRAWINGS

Some of the embodiments will be described in detail, with reference to the following figures, wherein like designations denote like members, wherein.

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 1:
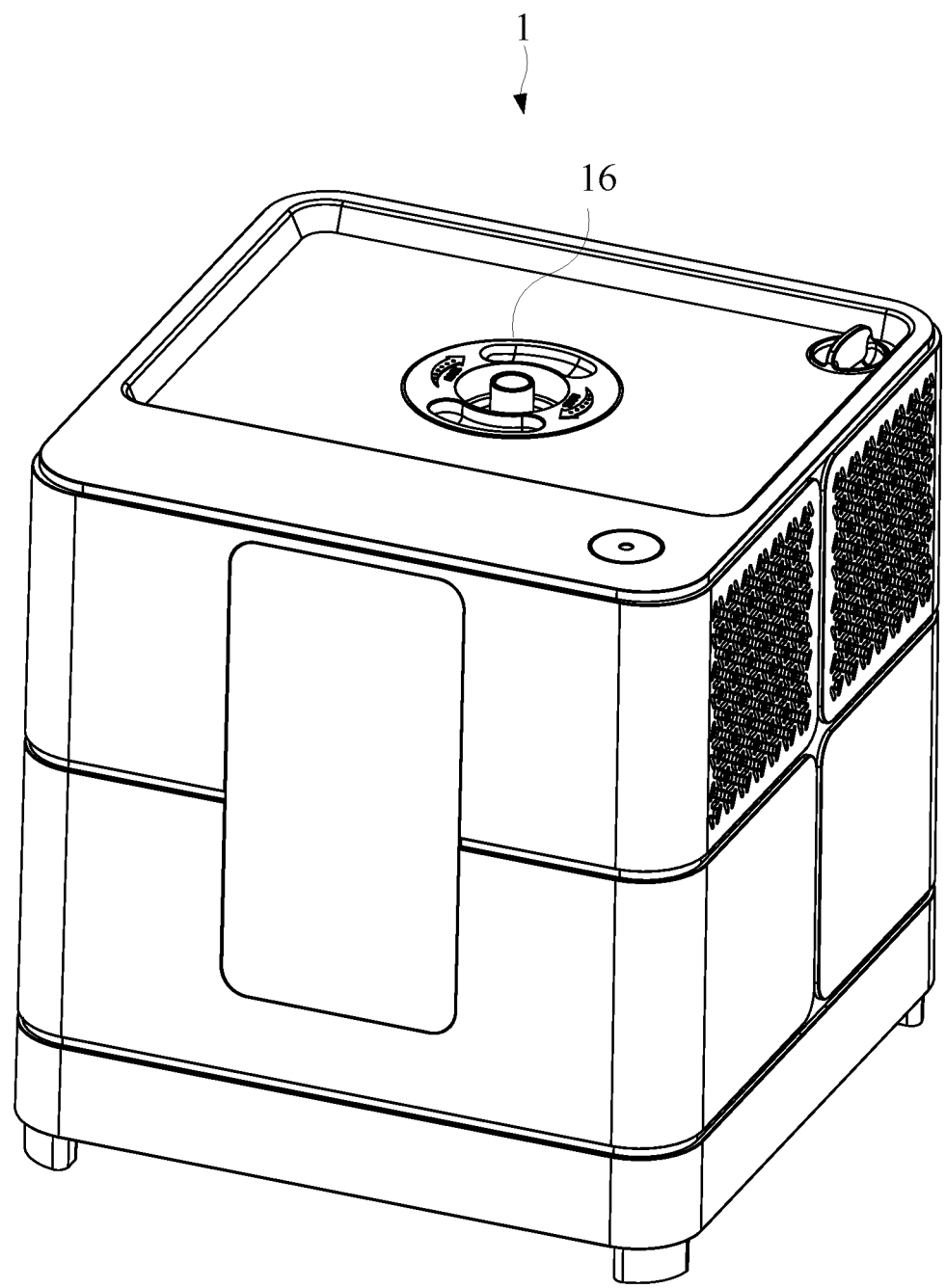
FIG. 1 shows a schematic diagram of the gas generator in one embodiment of the present invention.
Figure 2:
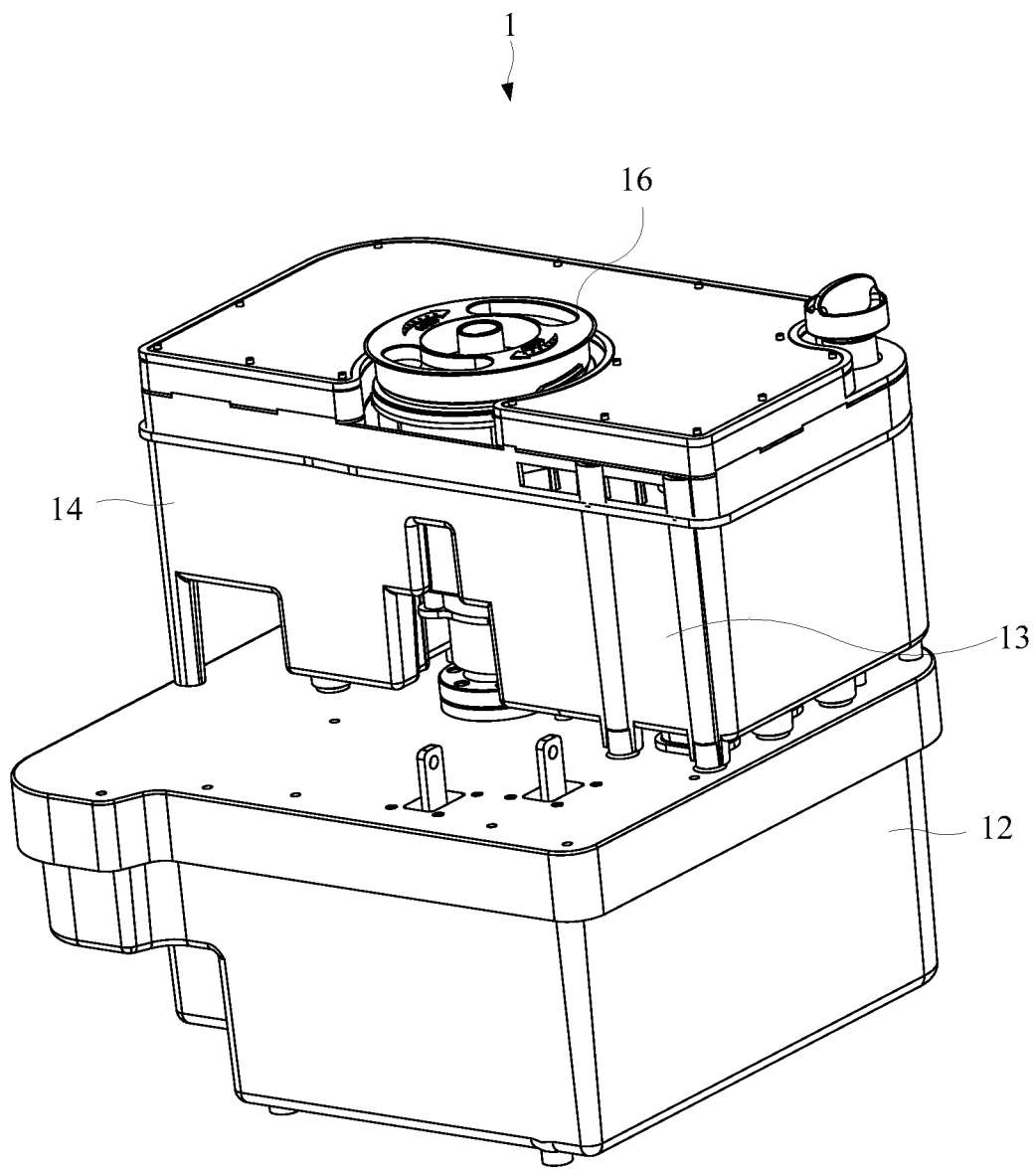
FIG. 2 shows a schematic diagram of the electrolytic cell and the humidification device of the gas generator in one embodiment of the present invention.
Figure 3:
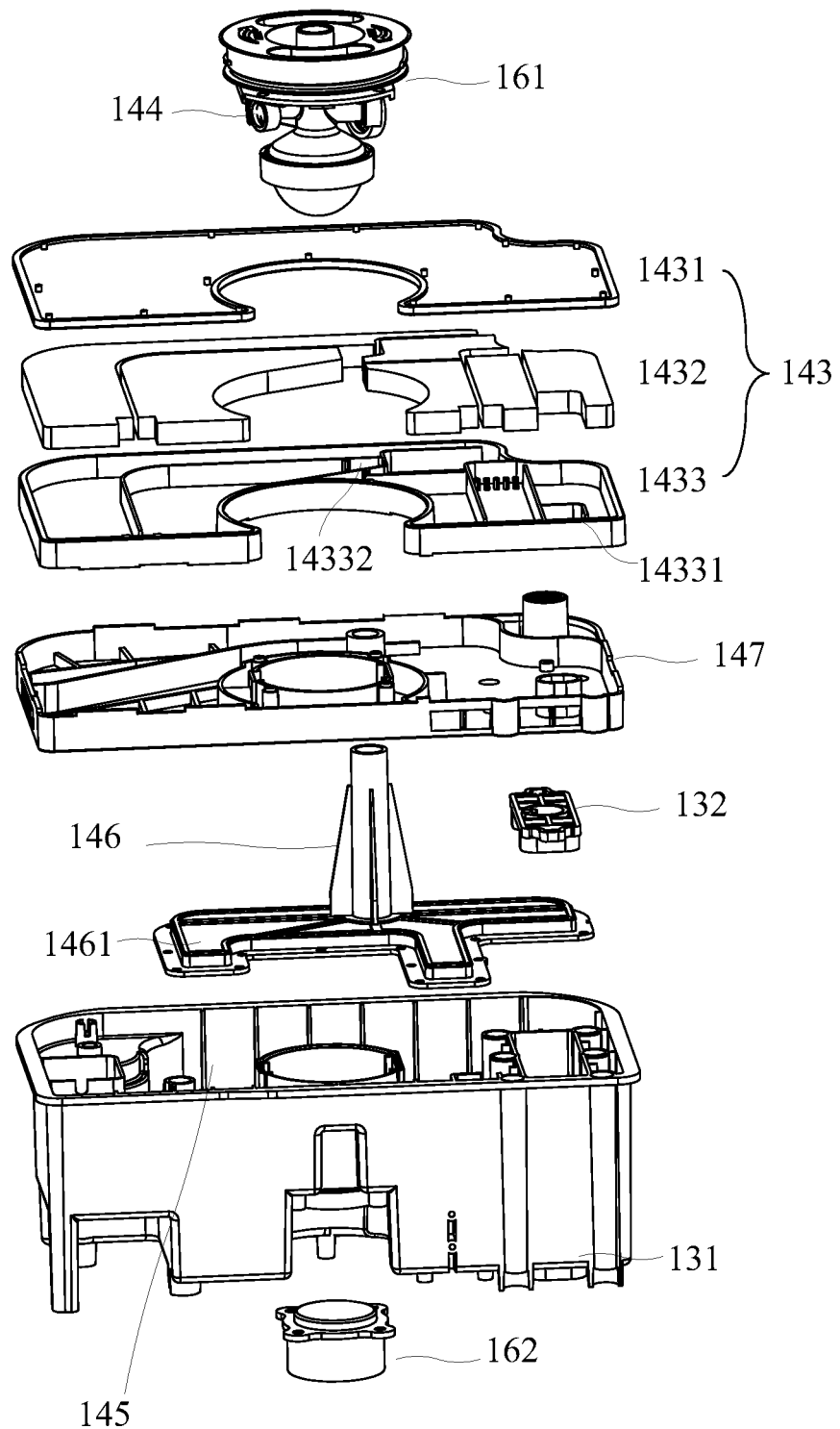
FIG. 3 shows an explosion diagram of the humidification device and the atomizing device of the gas generator in one embodiment of the present invention.
Figure 4:
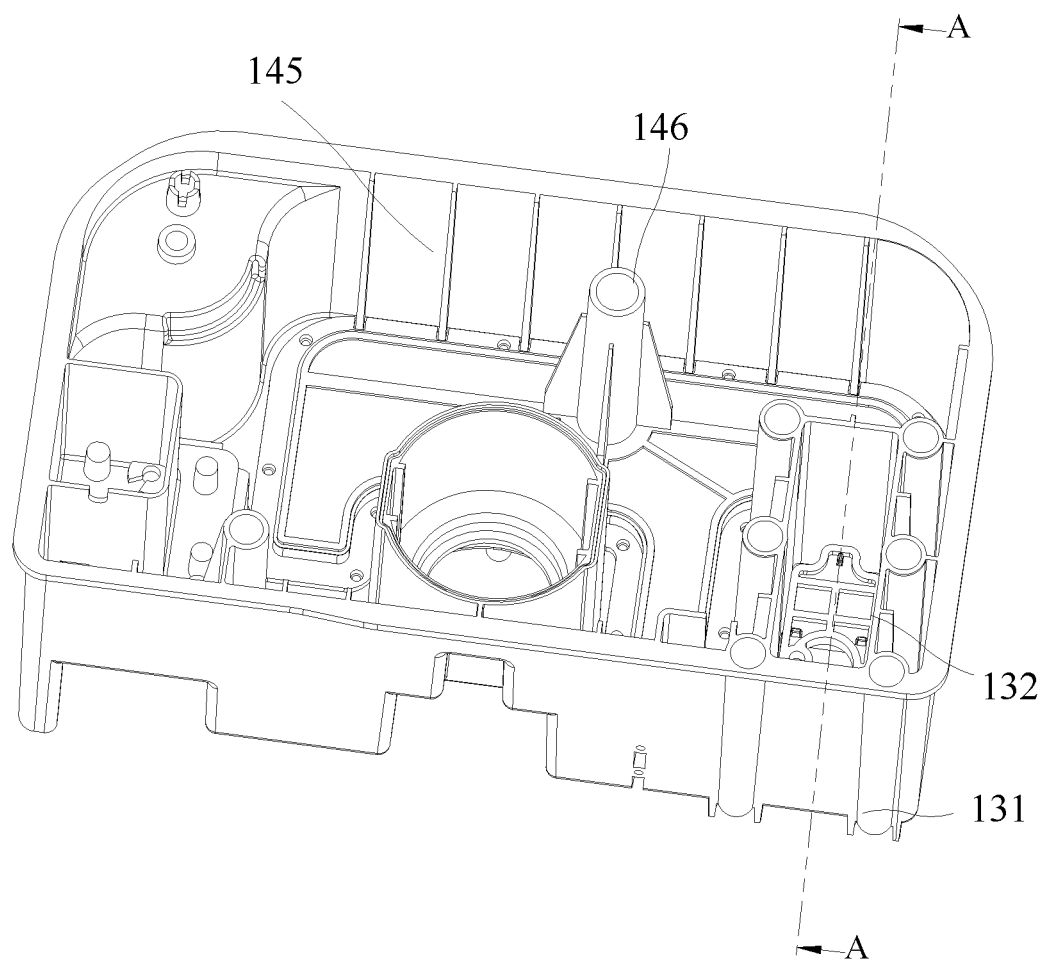
FIG. 4 shows a schematic diagram of the part of the water-blocking device of the gas generator in one embodiment of the present invention.
Figure 5:
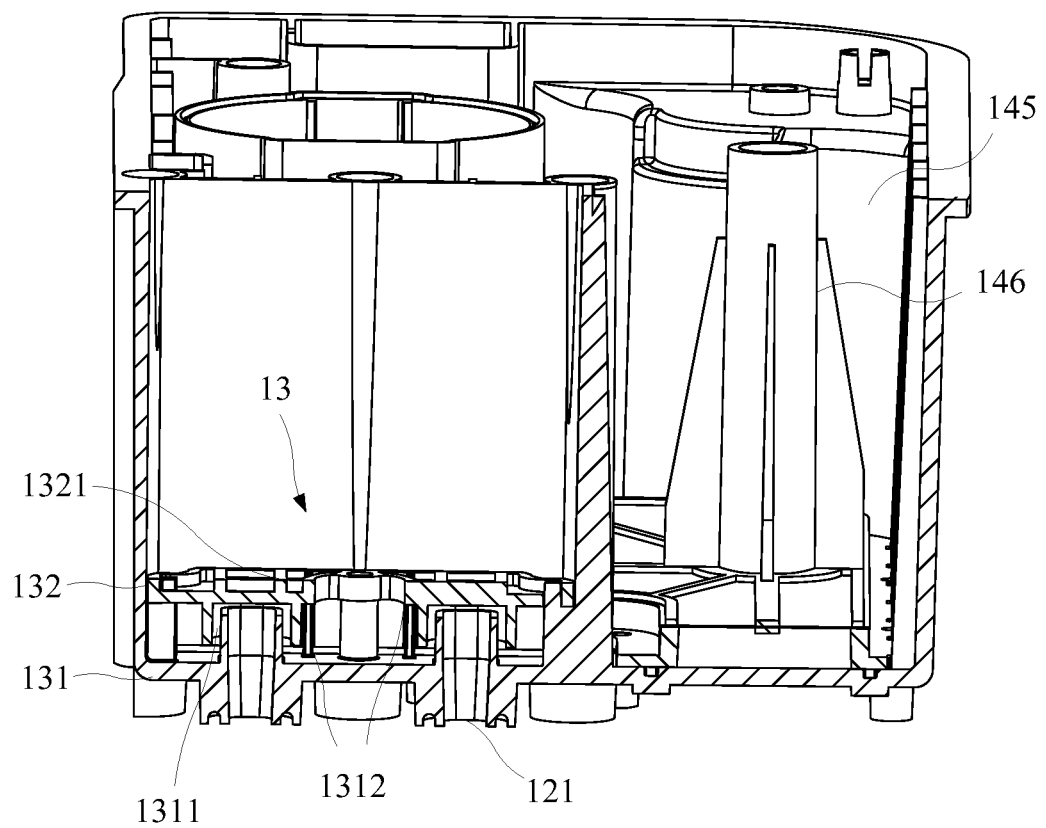
FIG. 5 shows a cross-section diagram crossing along the A-A line of the gas generator in the embodiment shown in FIG. 4 of the present invention.

Please refer to FIG. 1 to FIG. 5. FIG. 1 shows a schematic diagram of the gas generator 1 in one embodiment of the present invention; FIG. 2 shows a schematic diagram of the electrolytic cell 12 and the humidification device 14 of the gas generator 1 in one embodiment of the present invention; FIG. 3 shows an explosion diagram of the humidification device 14 and the atomizing device 16 of the gas generator 1 in one embodiment of the present invention; FIG. 4 shows a schematic diagram of the part of the water-blocking device 13 of the gas generator 1 in one embodiment of the present invention; and FIG. 5 shows a cross-section diagram crossing along the A-A line of the gas generator 1 in the embodiment shown in FIG. 4 of the present invention. The present invention provides a gas generator 1 comprising an electrolytic cell 12 and a water-blocking device 13. The electrolytic cell 12 contains electrolyzed water, wherein the electrolyzed water includes an electrolyte. The electrolytic cell 12 is used for electrolyzing the electrolyzed water to generate a gas with hydrogen, and the electrolytic cell 12 has an outlet 121 for outputting the gas with hydrogen. The water-blocking device 13 is configured on the outlet 121, wherein the water-blocking device 131 is used for preventing the electrolyzed water from flowing out of the electrolytic cell 12 when the electrolytic cell 12 is tilted by a tilt angle.

The water-blocking device 13 comprises a bottom 131 and a leakproof part 132, and the bottom 131 has an inlet 1311 for receiving the gas with hydrogen, and the inlet 1311 is closed selectively by the leakproof part 132 for preventing the electrolyzed water from flowing out of the electrolytic cell 12. Furthermore, the bottom 131 has an elastic plug 1312, and the leakproof part 132 has a plug hole 1321, and the elastic plug 1312 is coupled with the plug hole 1321 to make the inlet 1311 to be closed selectively by the leakproof part 132 for preventing the electrolyzed water from flowing out of the electrolytic cell 12, wherein the tilt angle is over than 90 degrees.

In practical application, the water-blocking device 13 comprises a bottom 131 and a leakproof part 132, and the bottom 131 has an inlet 1311 and an elastic plug 1312, and the inlet 1311 is connected to the outlet 121 for receiving the gas with hydrogen. The leakproof part 132 has a plug hole 1321, and the elastic plug 1312 is set on the plug hole 1321 with recoverability for keeping the inlet 1311 open by supporting the leakproof part 132. When the electrolytic cell 12 is tilted over than the tilt angle, the elastic plug 1312 will be compressed and slide into the plug hole 1321 to make the leakproof part 132 be coupled with the bottom 131, thereby further closing the inlet 1311 for preventing the electrolyzed water from flowing out of the electrolytic cell 12.

Figure 6:
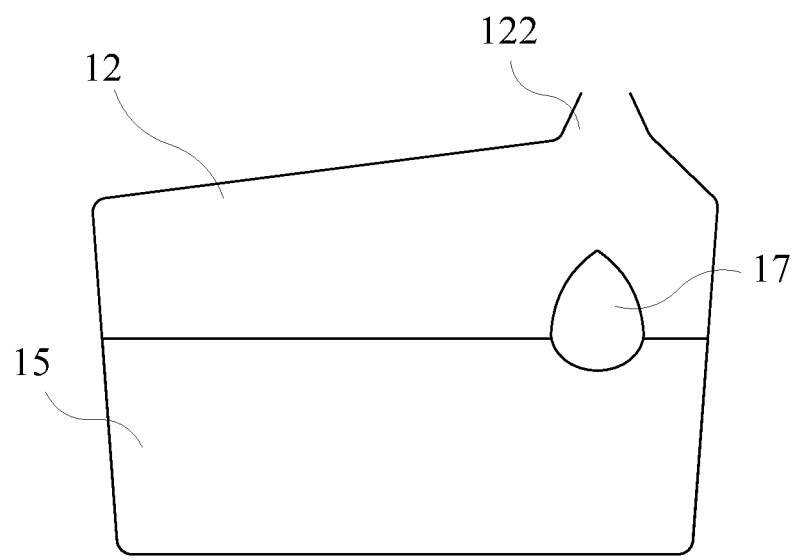
FIG. 6 shows a schematic diagram of the electrolytic cell and the float of the gas generator in one embodiment of the present invention.
Figure 7:
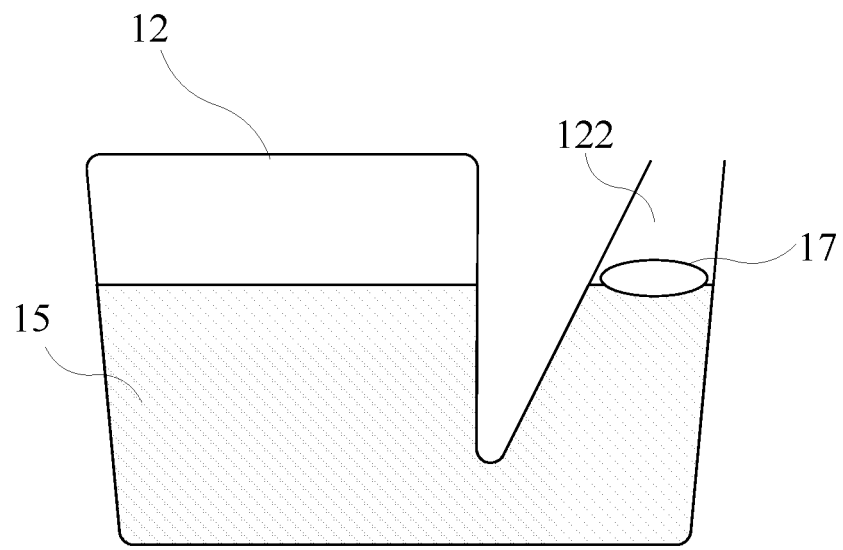
FIG. 7 shows a schematic diagram of the electrolytic cell and the float of the gas generator in another embodiment of the present invention.

Please refer to FIG. 6 and FIG. 7. FIG. 6 shows a schematic diagram of the electrolytic cell 12 and the float 17 of the gas generator 1 in one embodiment of the present invention, and FIG. 7 shows a schematic diagram of the electrolytic cell 12 and the float 17 of the gas generator 1 in another embodiment of the present invention. In one embodiment, the electrolytic cell 12 has a water charging channel 122 for charging the electrolyzed water 15 into the electrolytic cell 12, and a float 17 contained in the electrolytic cell 12, wherein the water charging channel 122 will be blocked by the float 17 when a level of the electrolyzed water 15 in the electrolytic cell 12 is higher than a predetermined height, so that the electrolyzed water 15 will not be overcharged into the electrolytic cell 12. In addition, the float 17 also prevent the electrolyzed water 15 from flowing out of the electrolytic cell 12 through the water charging channel 122 when the electrolytic cell 12 is tilted or any other condition causes the level of the electrolyzed water rises. Furthermore, the water charging channel 122 has an outward tapering portion, wherein a minimum inner diameter of the portion is smaller than a maximum outer diameter of the float 17, so that the water charging channel 122 will be blocked by the float 17 when the level of the electrolyzed water 15 in the electrolytic cell 12 is higher than the predetermined height. In one embodiment, the float is contained in the water charging channel 122 directly. In practical application, the electrolytic cell 12 can be a conical container, so that the float 17 can move to the water charging channel 122 by the shape of the electrolytic cell 12 and block the water charging channel 122 easily when the level of the electrolyzed water 15 rises. In another embodiment, the electrolytic cell 12 has a specifically geometric appearance for limiting the movement of the float 17, so that the movement path of the float 17 will be restricted in a specific area.

The float 17 can block the water charging channel 122 easily by the limitation from the electrolytic cell 12 when the level of the electrolyzed water 15 rises, which can prevent the float 17 from being too far away from the water charging channel 122 so that the water charging channel 122 cannot be blocked by the float 17. In another embodiment, the float 17 is limited nearly to the water charging channel 122 by a fitting (like rails corresponding to the float 17 or a connected line) wherein the water charging channel 122 can be blocked easily by the float 17 when the level rises.

In practical application, for reducing the amount of the vent on the electrolytic cell 12, the water charging channel 122 can be connected to the outlet 121. The outlet 121 outputs the gas with hydrogen when the gas generator generates the gas with hydrogen, and can be used to charge the electrolyzed water 15 into the electrolytic cell 12 when the electrolytic cell 12 needs. In practical application, the float 17 can be made by a breathable material, so that the electrolytic cell 12 can maintain the inside pressure by the float 17 wherein the gas with hydrogen in the electrolytic cell 12 can be outputted through the float 17 when the water charging channel 122 is blocked. In addition, the float 17 can have a specifically geometric appearance for being coupled with the water charging channel 122, so that the water charging channel 122 can be blocked easily by the float 17. Furthermore, the predetermined height to block the water charging channel 122 can be decided by different geometric appearances of the float 17.

Please refer the FIG. 3 again; the gas generator 1 further comprises a humidification device 14 and an atomizing device 16, wherein the humidification device 14 is connected to the water-blocking device 13 for receiving and moisturizing the gas with hydrogen, and the atomizing device 16 is connected to the humidification device 14 for receiving the gas with hydrogen. The atomizing device 16 further generates an atomized gas to be mixed with the gas with hydrogen to generate a healthy gas, wherein the atomized gas is selected from a group comprising water vapor, an atomizing solution, a volatile essential oil, and any combination thereof.

The atomizing device 16 comprises an atomization chamber 161 and an oscillator 162, and the atomization chamber 161 is used to carry a precursor of the atomized gas and to mix the atomized gas with the gas with hydrogen to generate the healthy gas. The oscillator 162 is configured under the atomization chamber 161 and used for oscillating and atomizing the precursor of the atomized gas to generate the atomized gas required. In addition, the atomizing device 16 can comprise a gas flow valve to control the flow rate of the healthy gas so that humans can adjust the intake.

Furthermore, the humidification device 14 comprises a cooling filter element 143 and a vent 144, and the cooling filter element 143 is used for cooling the gas with hydrogen and generating a filtered gas with hydrogen by filtering out impurities from the gas with hydrogen, and the vent 144 is used for outputting the filtered gas with hydrogen into the atomizing device 16, wherein the impurity can be electrolyte in the electrolyzed water.

Besides, the cooling filter element 143 can comprise a top filtered cup 1431, a cooling filter 1432, and a bottom filtered cup 1433. The cooling filter 1432 is configured between the top filtered cup 1431 and the bottom filtered cup 1433, and the cooling filter 1432 is used for filtering out impurities in the gas with hydrogen, wherein the cooling filter 1432 can be asbestos. Furthermore, the bottom filtered cup 1433 has a filtering inlet 14331 and a filtering outlet 14332, and the filtering inlet 14331 is used to input the gas with hydrogen from the inlet 1311 to the cooling filter element 143, and the filtering outlet 14332 is used to output the filtered gas with hydrogen to the outside of the cooling filter element 143.

The humidification device 14 has a shell 145 containing a humidification liquid, and the humidification device 14 further comprises an intake element 146 coupled with the cooling filter element 143 for passing the filtered gas with hydrogen into the humidification liquid. The filtered gas with hydrogen is passed through the humidification liquid to be further filtered and humidified and then outputted to the vent 144, wherein the humidification liquid can be running water or drinking water. Furthermore, the intake element 146 comprises an inlet screen 1461 for further filtering the filtered gas with hydrogen before the filtered gas with hydrogen being passed into the humidification liquid, wherein the inlet screen 1461 can be a unidirectional screen to prevent the humidification liquid from flowing into the intake element 146. In addition, the humidification device 14 can comprise a top cover 147, and the top cover 147 is used to separate the cooling filter element 143 from others.

Figure 8:
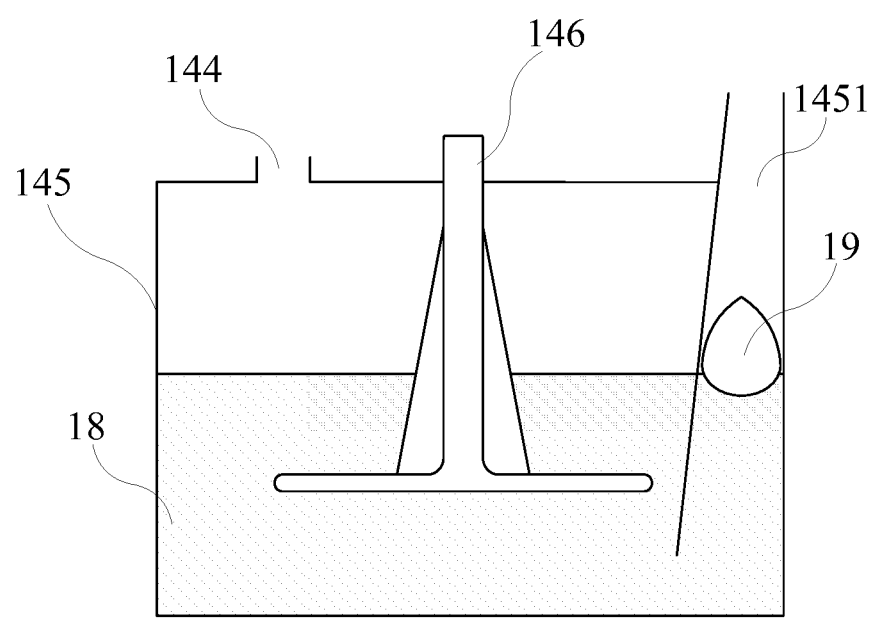
FIG. 8 shows a schematic diagram of the shell of the humidification device and the float of the gas generator in one embodiment of the present invention.

Please refer to FIG. 8. FIG. 8 shows a schematic diagram of the shell 145 of the humidification device 14 and the float 19 of the gas generator 1 in one embodiment of the present invention. In one embodiment, the shell 145 of the humidification device 14 has a water charging channel 1451, wherein the water charging channel 1451 is used for charging the humidification liquid 18 into the shell 145. A float 19 is contained in the shell 145, and the water charging channel 1451 will be blocked by the float 19 when a level of the humidification liquid 18 in the shell 145 is higher than a predetermined height, so that the humidification liquid 18 will not be overcharged into the shell 145. In addition, the float 19 also prevent the humidification liquid 18 from flowing out of the shell 145 through the water charging channel 1451 when the shell 145 is tilted or any other condition causes the level of the humidification liquid 18 rises. Furthermore, the water charging channel 1451 has an outward tapering portion, wherein a minimum inner diameter of the portion is smaller than a maximum outer diameter of the float 19, so that the water charging channel 1451 will be blocked by the float 19 when the level of the humidification liquid 18 in the shell 145 is higher than the predetermined height. In one embodiment, the float 19 is contained in the water charging channel 1451 directly. In practical application, the shell 145 can be a conical container, so that the float 19 can move to the water charging channel 1451 by the shape of the shell 145 and block the water charging channel 1451 easily when the level of the humidification liquid 18 rises.

In another embodiment, the shell 145 has a specifically geometric appearance for limiting the movement of the float 19, so that the movement path of the float 19 will be restricted in a specific area. The float 19 can block the water charging channel 1451 easily by the limitation from the shell 145 when the level of the humidification liquid 18 rises. In another embodiment, the float 19 is limited nearly to the water charging channel 1451 by a fitting (like rails corresponding to the float 19 or a connected line), wherein the water charging channel 1451 can be blocked easily by the float 19 when the level rises.

In practical application, for reducing the amount of the vent on the shell 145, the water charging channel 1451 can be connected to the vent 144. The vent 144 outputs the filtered gas with hydrogen when the gas generator generates the gas with hydrogen, and can be used to charge the humidification liquid 18 into the shell 145 when the humidification device 14 needs. In practical application, the float 19 can be made by a breathable material, so that the humidification device 14 can maintain the inside pressure by the float 19 wherein the filtered gas with hydrogen in the shell 145 can be outputted through the float 19 when the water charging channel 1451 is blocked. In another embodiment, the water charging channel 1451 is coupled to the cooling filter element 143 for receiving the filtered gas with hydrogen. In addition, the float 19 can have a specifically geometric appearance for coupling with the water charging channel 1451, so that the water charging channel 1451 can be blocked easily by the float 19. Furthermore, the predetermined height to block the water charging channel 1451 can be decided by different geometric appearances of the float 19.

In conclusion, the priority of the present invention is to provide a gas generator comprising an electrolytic cell and a humidification device. In the gas generator of the present invention, the electrolytic cell is used for electrolyzing electrolyzed water to generate a gas with hydrogen, and the humidification device is used for filtering and humidifying the gas with hydrogen for providing humans to breathe, wherein the gate of the electrolytic cell will be closed to prevent the electrolyzed water from flowing out of the electrolytic cell when the gas generator is toppled.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A gas generator, comprising:
   an electrolytic cell configured for electrolyzing an electrolyzed water to generate a gas with hydrogen;
   a shell vertically stacking above the electrolytic cell, the shell configured for containing a humidification liquid;
   a top cover vertically stacking above the shell; and
   a filter element vertically stacking above the top cover and configured for filtering out impurities in the gas with hydrogen;
   wherein the top cover separates the filter element from the shell, and the filter element is vertically spaced apart from the shell; wherein an intake element is located in the shell and coupled with the filter element for passing the filtered gas with hydrogen into the humidification liquid.

2. The gas generator of claim 1, wherein the filter element comprises a top filtered cup, a bottom filtered cup, and a cooling filter between the top filtered cup and the bottom filtered cup, the cooling filter is used for filtering out the impurities in the gas with hydrogen.

3. The gas generator of claim 2, wherein the bottom filtered cup has a filtering inlet and a filtering outlet located on the same plane, the filtering inlet is used to receiving the gas with hydrogen from the electrolytic cell, and the filtering outlet is used to output the filtered gas with hydrogen to the intake element located in the shell.

4. The gas generator of claim 2, wherein the cooling filter comprising a plurality of sub-filters separate from each other by a plurality of partitions of the bottom filtered cup.

5. The gas generator of claim 1, wherein the intake element comprises an inlet screen for further filtering the filtered gas with hydrogen before the filtered gas with hydrogen being passed into the humidification liquid.

6. The gas generator of claim 1, further comprising an atomizing device surround by the shell and the filter element, the atomizing device configured for generating an atomized gas to be mixed with the filtered gas with hydrogen to generate a healthy gas.

7. The gas generator of claim 6, wherein the atomizing device comprises an atomization chamber and an oscillator, the atomization chamber is used to mix the atomized gas with the filtered gas with hydrogen to generate the healthy gas, and the oscillator is configured under the atomization chamber and located within a hollow of the shell.

* * * * *